(12) United States Patent  
Sharma

(10) Patent No.: US 9,037,244 B2  
(45) Date of Patent: May 19, 2015

(54) METHOD AND APPARATUS FOR ELECTRICAL STIMULATION OF THE PANCREATICO-BILIARY SYSTEM

(76) Inventor: Virender K. Sharma, Paradise Valley, AZ (US)

( * ) Notice: Subject to any disclaimer, the term of this patent is extended or adjusted under 35 U.S.C. 154(b) by 1237 days.

(21) Appl. No.: 12/030,222

(22) Filed: Feb. 13, 2008

(65) Prior Publication Data

US 2008/0195171 A1    Aug. 14, 2008

Related U.S. Application Data

(60) Provisional application No. 60/889,569, filed on Feb. 13, 2007.

(51) Int. Cl.
| | | |
|---|---|---|
| *A61N 1/00* | (2006.01) | |
| *A61N 1/05* | (2006.01) | |
| *A61N 1/36* | (2006.01) | |
| *A61N 1/08* | (2006.01) | |

(52) U.S. Cl.
CPC ... *A61N 1/05* (2013.01); *A61N 1/08* (2013.01); *A61N 1/36007* (2013.01)

(58) Field of Classification Search
CPC ............ A61B 5/42; A61N 1/00; A61N 1/02; A61N 1/04; A61N 1/08; A61N 1/10; A61N 1/11; A61N 1/12; A61N 1/13; A61N 1/14; A61N 1/15; A61N 1/16; A61N 1/18; A61N 1/3605; A61N 1/37205

See application file for complete search history.

(56) References Cited

U.S. PATENT DOCUMENTS

| | | |
|---|---|---|
| 3,814,080 A | 6/1974 | Norman |
| 3,916,875 A | 11/1975 | Toch |
| 4,792,330 A | 12/1988 | Lazarus et al. |
| 4,957,484 A | 9/1990 | Murtfeldt |
| 5,188,104 A | 2/1993 | Wernicke et al. |
| 5,231,988 A | 8/1993 | Wernicke et al. |
| 5,263,480 A | 11/1993 | Wernicke et al. |
| 5,305,745 A | 4/1994 | Zacouto |
| 5,387,231 A | 2/1995 | Sporer |

(Continued)

FOREIGN PATENT DOCUMENTS

| | | |
|---|---|---|
| EP | 1504778 | 9/2007 |
| WO | WO9314694 | 8/1993 |

(Continued)

OTHER PUBLICATIONS

Examiner's first report on Australian Patent Application No. 2008216316, dated Dec. 16, 2010.

(Continued)

*Primary Examiner* — Christopher D Koharski  
*Assistant Examiner* — Elizabeth K So  
(74) *Attorney, Agent, or Firm* — Novel IP

(57) ABSTRACT

The present invention is directed to a method and apparatus for electrical stimulation of the pancreatico-biliary system. Electrode sets are placed in the pancreatico-biliary system in an arrangement that induce contractions or relaxation of the portion or whole of the pancreatico-biliary system by electrical stimulation of the surrounding tissue, muscles and nerves. The electrical stimulus is applied for periods of varying duration and varying frequency so as to produce the desired therapeutic effect, including inhibiting fat digestion or fat absorption by a patient and inducing satiety in the patient.

20 Claims, 8 Drawing Sheets

(56) References Cited

U.S. PATENT DOCUMENTS

| | | |
|---|---|---|
| 5,391,143 A | 2/1995 | Kensey |
| 5,423,872 A | 6/1995 | Cigaina |
| 5,655,548 A | 8/1997 | Nelson et al. |
| 5,690,691 A | 11/1997 | Chen et al. |
| 5,836,994 A | 11/1998 | Bourgeois |
| 5,861,014 A | 1/1999 | Familoni |
| 5,861,044 A | 1/1999 | Crenshaw |
| 5,865,744 A | 2/1999 | Lemelson |
| 6,024,704 A | 2/2000 | Meador et al. |
| 6,041,258 A | 3/2000 | Cigaina et al. |
| 6,106,477 A | 8/2000 | Miesel et al. |
| 6,115,637 A | 9/2000 | Lennox et al. |
| 6,129,685 A | 10/2000 | Howard, III |
| 6,238,423 B1 | 5/2001 | Bardy |
| 6,272,370 B1 | 8/2001 | Gillies et al. |
| 6,292,695 B1 | 9/2001 | Webster, Jr. et al. |
| 6,321,109 B2 | 11/2001 | Ben-Haim et al. |
| 6,321,124 B1 | 11/2001 | Cigaina |
| 6,368,274 B1 | 4/2002 | Van Antwerp et al. |
| 6,370,417 B1 | 4/2002 | Horbaschek et al. |
| 6,475,223 B1 | 11/2002 | Werp et al. |
| 6,510,332 B1 | 1/2003 | Greenstein |
| 6,535,764 B2 | 3/2003 | Imran et al. |
| 6,542,776 B1 | 4/2003 | Gordon et al. |
| 6,587,719 B1 | 7/2003 | Barrett et al. |
| 6,606,523 B1 | 8/2003 | Jenkins |
| 6,609,025 B2 | 8/2003 | Barrett et al. |
| 6,611,715 B1 | 8/2003 | Boveja |
| 6,615,084 B1 | 9/2003 | Cigaina |
| 6,676,686 B2 | 1/2004 | Naganuma |
| 6,678,557 B1 | 1/2004 | Tumey |
| 6,684,104 B2 | 1/2004 | Gordon et al. |
| 6,685,729 B2 | 2/2004 | Gonzalez |
| 6,741,882 B2 | 5/2004 | Schaffter et al. |
| 6,826,428 B1 | 11/2004 | Chen et al. |
| 6,832,114 B1 | 12/2004 | Whitehurst et al. |
| 6,865,416 B2 | 3/2005 | Dev et al. |
| 6,879,859 B1 | 4/2005 | Boveja |
| 6,889,076 B2 | 5/2005 | Cigaina |
| 6,895,278 B1 | 5/2005 | Gordon |
| 6,901,295 B2 | 5/2005 | Sharma |
| 6,918,873 B1 | 7/2005 | Millar et al. |
| 6,934,583 B2 | 8/2005 | Weinberg et al. |
| 6,947,792 B2* | 9/2005 | Ben-Haim et al. ............... 607/2 |
| 6,950,707 B2 | 9/2005 | Whitehurst |
| 6,961,621 B2 | 11/2005 | Krishnan et al. |
| 6,970,746 B2 | 11/2005 | Eckmiller et al. |
| 7,006,871 B1 | 2/2006 | Darvish et al. |
| 7,054,690 B2 | 5/2006 | Imran |
| 7,076,306 B2 | 7/2006 | Marchal et al. |
| 7,177,693 B2 | 2/2007 | Starkebaum |
| 7,194,301 B2 | 3/2007 | Jenkins et al. |
| 7,200,443 B2 | 4/2007 | Faul |
| 7,299,091 B2 | 11/2007 | Barrett et al. |
| 7,320,675 B2 | 1/2008 | Pastore et al. |
| 7,324,852 B2 | 1/2008 | Barolat et al. |
| 7,340,306 B2 | 3/2008 | Barrett et al. |
| 7,418,292 B2 | 8/2008 | Shafer |
| 7,445,630 B2 | 11/2008 | Lashinski et al. |
| 7,481,759 B2 | 1/2009 | Whitehurst et al. |
| 7,519,421 B2 | 4/2009 | Denker et al. |
| 7,526,337 B2 | 4/2009 | Shuros et al. |
| 7,551,964 B2 | 6/2009 | Dobak, III |
| 7,596,413 B2 | 9/2009 | Libbus et al. |
| 7,632,234 B2 | 12/2009 | Manda et al. |
| 7,653,438 B2 | 1/2010 | Deem et al. |
| 7,664,548 B2 | 2/2010 | Amurthur et al. |
| 7,689,276 B2 | 3/2010 | Dobak |
| 7,734,341 B2* | 6/2010 | Shuros ............... 607/2 |
| 7,761,166 B2 | 7/2010 | Giftakis et al. |
| 7,803,195 B2 | 9/2010 | Levy et al. |
| 7,881,797 B2 | 2/2011 | Griffin et al. |
| 7,894,906 B2 | 2/2011 | Shuros |
| 7,901,419 B2 | 3/2011 | Bachmann et al. |
| 7,917,208 B2 | 3/2011 | Yomtov et al. |
| 7,941,221 B2 | 5/2011 | Foley |
| 8,126,538 B2 | 2/2012 | Shuros et al. |
| 8,346,482 B2 | 1/2013 | Fernandez |
| 2001/0041870 A1 | 11/2001 | Gillis et al. |
| 2002/0029037 A1 | 3/2002 | Kim |
| 2002/0072780 A1 | 6/2002 | Foley |
| 2002/0123674 A1 | 9/2002 | Plicchi et al. |
| 2002/0188253 A1 | 12/2002 | Gordon et al. |
| 2003/0113303 A1 | 6/2003 | Schwartz |
| 2003/0114895 A1 | 6/2003 | Gordon et al. |
| 2003/0144708 A1 | 7/2003 | Starkebaum |
| 2003/0204185 A1 | 10/2003 | Sherman et al. |
| 2004/0015201 A1 | 1/2004 | Greenstein |
| 2004/0088022 A1 | 5/2004 | Chen |
| 2004/0102804 A1 | 5/2004 | Chin |
| 2004/0147976 A1 | 7/2004 | Gordon et al. |
| 2004/0158297 A1 | 8/2004 | Gonzalez |
| 2004/0167583 A1* | 8/2004 | Knudson et al. ............... 607/40 |
| 2004/0172102 A1 | 9/2004 | Leysieffer |
| 2004/0193229 A1 | 9/2004 | Starkebaum et al. |
| 2004/0210118 A1 | 10/2004 | Letort |
| 2005/0070974 A1 | 3/2005 | Knudson et al. |
| 2005/0075702 A1 | 4/2005 | Shafer |
| 2005/0143787 A1 | 6/2005 | Boveja et al. |
| 2005/0149014 A1 | 7/2005 | Hauck et al. |
| 2005/0149142 A1 | 7/2005 | Starkebaum |
| 2005/0149157 A1 | 7/2005 | Hunter et al. |
| 2005/0222637 A1* | 10/2005 | Chen ............... 607/40 |
| 2005/0222638 A1 | 10/2005 | Foley et al. |
| 2005/0240239 A1 | 10/2005 | Boveja et al. |
| 2005/0267440 A1 | 12/2005 | Herman et al. |
| 2006/0074453 A1 | 4/2006 | Kieval et al. |
| 2007/0021731 A1 | 1/2007 | Garibaldi et al. |
| 2007/0244520 A1 | 10/2007 | Ferren et al. |
| 2007/0282376 A1 | 12/2007 | Shuros et al. |
| 2008/0097412 A1 | 4/2008 | Shuros et al. |
| 2008/0294228 A1 | 11/2008 | Brooke et al. |
| 2009/0062881 A1* | 3/2009 | Gross et al. ............... 607/40 |
| 2009/0228059 A1 | 9/2009 | Shuros et al. |

FOREIGN PATENT DOCUMENTS

| | | |
|---|---|---|
| WO | PCT/US98/10402 | 12/1998 |
| WO | PCT/US00/09910 | 10/2000 |
| WO | PCT/US00/10154 | 10/2000 |
| WO | WO2004006785 | 1/2004 |
| WO | WO2004006795 | 1/2004 |
| WO | WO2003098177 | 6/2004 |
| WO | WO2004032791 | 7/2004 |
| WO | WO2005089863 | 9/2005 |
| WO | WO2007067690 | 6/2007 |
| WO | WO2007146493 | 12/2007 |
| WO | WO2007146489 | 2/2008 |
| WO | WO2007146517 | 5/2008 |
| WO | WO2008030344 | 5/2008 |
| WO | WO2008100974 | 12/2009 |

OTHER PUBLICATIONS

International Search Report for PCT/US2008/053780, date of mailing, Jun. 8, 2009, V.K. Sharma.

Knott, E. M., et al., "Increased Lymphatic Flow in the Thoracic Duct During Manipulative Intervention", J Am Osteopath Assoc., 105(10), (Oct. 2005), 447-456.

Issa, Z. F., et al., "Thoracic Spinal Cord Stimulation Reduces the Risk of Ischemic Ventricular Arrhythmias in a Postinfarction Heart Failure Canine Model", Circulation, 111(24) (Jun. 21, 2005), 3217-3220.

International Application Serial No. PCT/US2007/018631, International Search Report mailed Mar. 25, 2008, 4 pgs.

International Application Serial No. PCT/US2007/018631, Written Opinion mailed Mar. 25, 2008, 7 pgs.

International Application Serial No. PCT/US2007/06178, International Search Report mailed Oct. 31, 2007, 5 pgs.

International Application Serial No. PCT/US2007/06178, Written Opinion mailed Oct. 31, 2007, 8 pgs.

(56) References Cited

OTHER PUBLICATIONS

PCT Application No. PCT/US2007/068617, International Search Report mailed Mar. 10, 2008, 4 pgs.

PCT Application No. PCT/US2007/068617, Written Opinion mailed Mar. 10, 2008, 8 pgs.

* cited by examiner

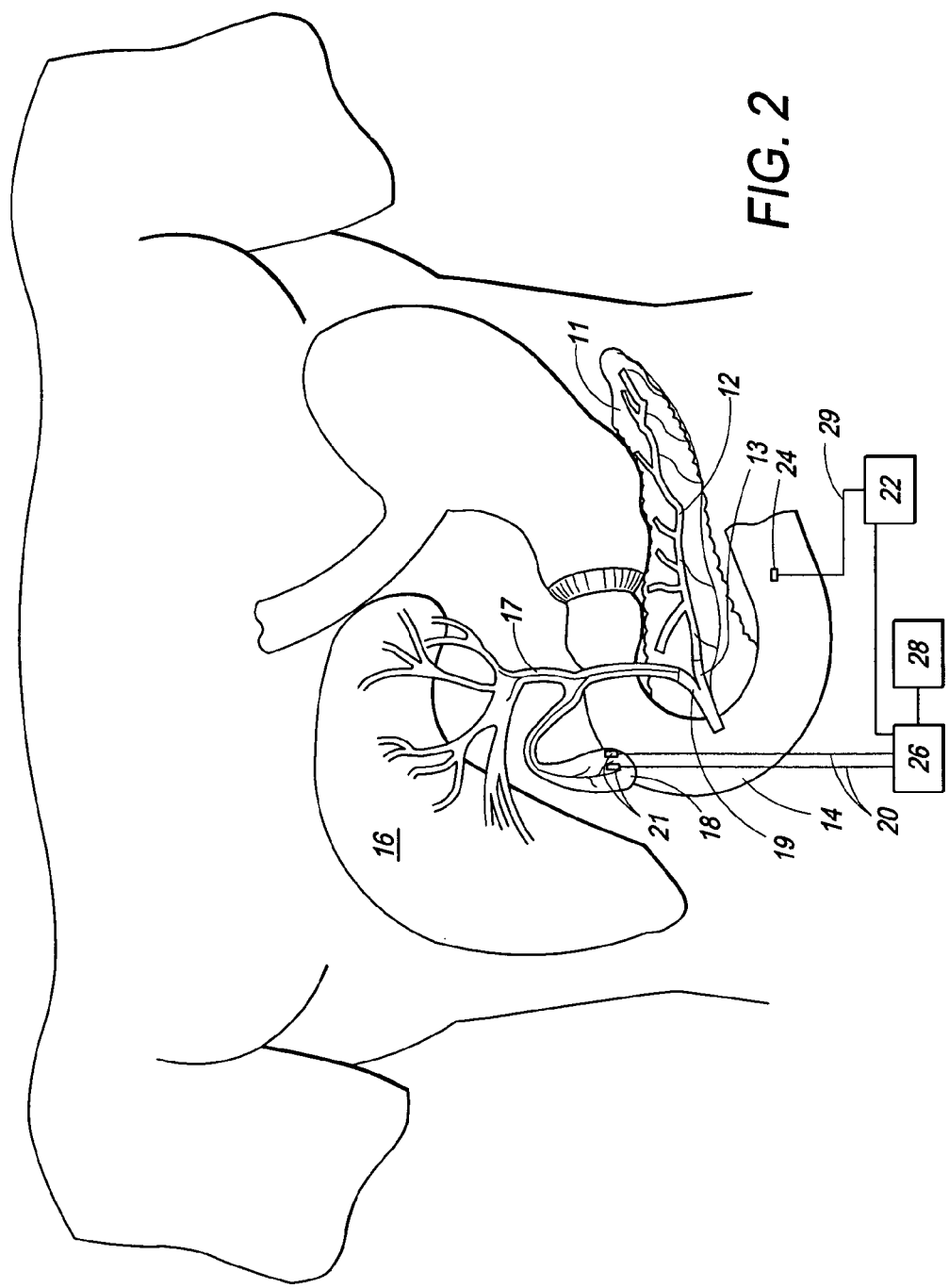

METHOD AND APPARATUS FOR ELECTRICAL STIMULATION OF THE PANCREATICO-BILIARY SYSTEM

CROSS-REFERENCE

This invention relies upon, for priority, U.S. Provisional Application No. 60/889,569, entitled "Method and Apparatus for Electrical Stimulation of the Pancreatico-Biliary System", filed on Feb. 13, 2007.

FIELD OF THE INVENTION

This invention relates generally to a method and apparatus for electrical stimulation of the pancreatico-biliary system. More particularly, this invention relates to a method and apparatus for treating a condition by electrically stimulating a portion of the pancreatico-biliary system where the portion is selected from the group consisting of the pancreas, pancreatic duct, bile duct, cystic duct, gall bladder, ampullary sphincter or nerves supplying the pancreatico-biliary system.

BACKGROUND OF THE INVENTION

As is generally known to those skilled in the art, diseases of pancreatico-biliary system are a common chronic condition affecting more than 10% of the population in the United States. Diseases of pancreatico-biliary system are associated with significant morbidity mortality, and impaired quality of life. These conditions result from motility disorders of the pancreatico-biliary system, which can lead to conditions like biliary colic, cholecystitis, choledocholithiasis, cholelithiasis, pancreatitis, pancreatic duct stone formations and chronic abdominal pain. In addition, diseases of the pancreatico-biliary system are associated with nutritional disorders such as under nutrition, obesity and high cholesterol.

Prior art approaches to treating certain diseases of the pancreatico-biliary system have numerous disadvantages. Used for the dissolution of choledocholithiasis, bile salts are cumbersome, expensive and not very effective. Open surgical or laparoscopic cholecystectomy can be used to treat choledocholithiasis and cholelithiasis and endoscopic procedures, including endoscopic retrograde cholangio-pancreaticography (ERCP), can be used for the management of pancreatic and biliary problems. However, these procedures are associated with significant morbidity and mortality in patients.

Current treatments for obesity include diet, exercise, behavioral treatments, medications, surgery (open and laproscopic) and endoscopic devices. In addition, there are currently a number of clinical trials on-going for treatments of obesity. For example, certain drugs being developed based on the chemistry of the hormone called Human Amylin, which plays a role in the regulation of appetite and food intake, have demonstrated an ability to cause a weight loss of 3.5 kg (7.7 lbs) over 60 weeks in mid-stage clinical trial results. While these drugs have shown signs of greater efficacy, a high efficacy pharmaceutical treatment has not yet been developed. Further, the issue of short-term and long-term side effects is always of concern to consumers, pharmaceutical providers and their insurers. Generally, diet or drug therapy programs have been consistency disappointing and fail to bring about significant, sustained weight loss in the majority of morbidly obese people.

Currently, most morbid obesity operations are, or include, gastric restrictive procedures, involving the creation of a small (15-35 ml) upper gastric pouch that drains through a small outlet (0.75-1.2 cm), setting in motion the body's satiety mechanism. About 15% of morbid obesity operations done in the United States involve gastric restrictive surgery combined with a malabsorptive procedure. This divides small intestinal flow into a biliary-pancreatic conduit and a food conduit. Potential long-term problems with surgical procedures are notorious, including those seen after any abdominal procedure, such as ventral hernia and small bowel obstruction, and those specific to bariatric procedures such as gastric outlet obstruction, fistula and stricture formation, marginal ulceration, protein malnutrition and vitamin deficiency. In addition there is a significant long-term failure with all bariatric surgical interventions.

Additionally, multiple endoscopic procedures for obesity are in development. Endoscopically placed gastric balloons restrict the gastric volume and result in satiety with smaller meals. Endoscopic procedures and devices to produce gastric pouch and gastrojejunal anastomosis to replicate laporoscopic procedures are also in development. These procedures, however, are not without their risks.

Gastric electric stimulation (GES) is another procedure that is currently in clinical trial. Gastric Electrical Stimulation (GES) employs an implantable, pacemaker-like device to deliver low-level electrical stimulation to the stomach. The procedure involves the surgeon suturing electrical leads to the outer lining of the stomach wall. The leads are then connected to the device, which is implanted just under the skin in the abdomen. Using an external programmer that communicates with the device, the surgeon establishes the level of electrical stimulation appropriate for the patient. The Transcend® implantable gastric stimulation device, manufactured by Transneuronix Corporation, is currently available in Europe for treatment of obesity.

The GES system consists of four components: a) an implanted pulse generator (neurostimulator), b) two unipolar intramuscular stomach leads, c) a stimulator programmer, and d) a memory cartridge. The neurostimulator used in the Enterra™ Therapy is a device that sends electrical pulses to the stomach and is approximately 2.5 inches (60 mm) long, 2 inches (50 mm) wide and 0.5 inches (12 mm) thick. The implantation of the gastric electrical stimulation device is done surgically under general anesthesia. A surgeon implants two small electrodes into the stomach muscle wall. Lead connectors are run subcutaneously along the abdomen and connected to the neurostimulator. The neurostimulator is placed beneath the skin in the abdomen, positioned below the rib cage and above the belt line. The programmer sets the stimulation parameters, which are typically set at an on time of 0.1 seconds alternating with an off time of 5.0 sec.

GES possibly causes weight loss by slowing the intrinsic electrical waves in the stomach through low-level electrical pulses. Animal studies have shown that this electrical stimulation causes the stomach to relax, resulting in distension of the stomach. This distension triggers nerves in the stomach involved in digestion to send signals via the central nervous system to the brain that the stomach is "full".

GES may also result in a decrease in gastro-intestinal hormones such as CCK, somatostatin GLP-1 and leptin, all of which are associated with hunger. In recent work, GES has shown promising results in obese patients. GES results in 35% EWL (excess weight loss) beyond 24 months and the results are sustained and replicated. This technology is currently available in Europe and Canada and undergoing trials for FDA approval in the U.S.

In another example, Medtronic offers for sale and use the Enterra™ Therapy, which is indicated for the treatment of chronic nausea and vomiting associated with gastroparesis when conventional drug therapies are not effective. The Enterra™ Therapy uses mild electrical pulses to stimulate the stomach. According to Medtronic, this electrical stimulation helps control the symptoms associated with gastroparesis including nausea and vomiting.

Several patent references teach the electrical stimulation of the stomach, such as U.S. Pat. No. 7,076,306 which teaches a method for stimulating the stomach of patient to decrease the pancreatic exocrine secretions. U.S. Pat. No. 7,006,871 teaches a method for stimulation of insulin producing portion of the pancreas, comprising: a glucose sensor, for sensing a level of glucose or insulin in a body serum; at least one electrode, for electrifying an insulin producing cell or group of cells; a power source for electing said at least one electrode with a pulse that does not initiate an action potential in said cell and has an effect of increasing insulin secretion; and a controller which receives the sensed level and controls said power source to electrify said at least one electrode to have a desired effect on said level. U.S. Pat. No. 6,832,114 teaches systems and methods for modulation of pancreatic endocrine secretion and treatment of diabetes and describes a method for stimulating the glucagon producing alpha cells thus inhibiting the release of glucagon and controlling diabetes. U.S. Pat. No. 5,231,988 teaches a method for the treatment of endocrine disorders by the stimulation of the vagus nerve. Blood sugar levels indicative of endocrine disorders triggers the stimulation of the patient's vagus nerve for modulation of electrical activity thereof to adjust secretion of endogenous insulin and thereby control the endocrine disorder.

U.S. Pat. No. 6,901,295, also assigned to inventor, discloses a device for electrical stimulation of a structure in the gastrointestinal tract wherein the device includes a pulse generator, a plurality of stimulating electrode sets connected through wires or wirelessly to the pulse generator and adapted to be positioned within or adjacent the structure or in contact with nerves innovating the structure, one more sensing electrodes for monitoring physiological parameters, and means for varying activity of the stimulating electrodes in response to change detected in the physiological parameters to thereby modify operation of the structure.

None of these prior art references teach the direct stimulation of pancreas, pancreatic duct or pancreatic sphincter to modulate pancreatic exocrine function or secretion or the stimulation of the biliary system to modulate biliary function or secretions.

SUMMARY OF THE INVENTION

Accordingly, it is a general object of the present invention to provide a method and apparatus for stimulating the pancreatico-biliary system which overcomes the problems encountered in the prior art methods.

It is an object of the present invention to provide a method and apparatus for modulating pancreatico-biliary muscle contractions with the intent of increasing pancreatico-biliary system pressure or tone or modulating pancreatico-biliary function.

It is also an object of the present invention to provide a method and apparatus for preventing ampullary sphincter relaxation and/or increasing the ampullary sphincter pressure or tone without causing permanent injury to the surrounding tissue or organs.

It is another object of the present invention to provide a method and apparatus for modulating pancreatico-biliary muscle contractions, preventing ampullary sphincter relaxation and/or increasing ampullary sphincter pressure or tone that is controllable by changing the duration, power and frequency of the stimulus without requiring subsequent endoscopic, surgical or radiological procedures.

It is another object of the present invention to provide a method and apparatus for treating disease of the pancreatico-biliary system by disrupting pancreatico-biliary contractions through any stimulation method, including reverse stimulation.

It is still another object of the present invention to provide a method and apparatus for treating disease of the pancreatico-biliary system including diseases of nutrition or other disorders by providing electrical stimulation to the pancreatico-biliary system through the use of one or more electrode set(s).

In accordance with these aims and objectives, the present invention is directed to a method and apparatus for electrical stimulation of the pancreatico-biliary system. Electrode sets are placed in the pancreatico-biliary system in an arrangement that induce contractions or relaxation of the portion or whole of the pancreatico-biliary system by electrical stimulation of the surrounding tissue, muscles and nerves. The electrical stimulus is applied for periods of varying duration and varying frequency so as to produce the desired therapeutic effect. The treatment may be short-term or may continue throughout the life of the patient in order to achieve the desired therapeutic effect. The stimulating electrode sets can be used either alone or in conjunction with other electrodes that sense change in a physiological parameter in the patient's body. The electrode sets can be placed endoscopically, surgically or radiologically.

In another embodiment, the present invention is directed toward a method for treating a biological condition, comprising the steps of arranging at least one electrode on at least one of a pancreas, a pancreatic duct, a pancreatic sphincter, a bile duct, a cystic duct, a gall bladder, a biliary sphincter, or autonomic nerves supplying the pancreas and the biliary system, and activating the electrode to provide an electrical stimulus thereto. The electrical stimulus may modulate the secretion of pancreatic juices into the small intestine. The electrical stimulus may modulate the secretion of bile juices into the small intestine. The electrical stimulus may cause the contraction of at least one of the pancreas, the pancreatic duct, the pancreatic sphincter, the bile duct, the cystic duct, the gall bladder, or the biliary sphincter. The electrical stimulus may relax at least one of the pancreas, the pancreatic duct, the pancreatic sphincter, the bile duct, the cystic duct, the gall bladder, or the biliary sphincter. The electrical stimulus may increase the tone of at least one of the pancreas, the pancreatic duct, the pancreatic sphincter, the bile duct, the gall bladder, or the biliary sphincter. The electrical stimulus is provided by a pulse generator and, optionally, in a frequency in the range of approximately of 1 mHz to 1 MHz.

In one embodiment, a method of the present invention further comprises the step of arranging at least one sensing electrode to detect a change in one or more physiological parameters. The physiological parameters are selected from the group consisting of esophageal peristalsis, esophageal pH, esophageal impedance, esophageal pressure, esophageal electrical activity, LES pressure, LES electrical activity, gastric peristalsis, gastric electrical activity, gastric chemical activity, gastric hormonal activity, gastric temperature, gastric pressure, gastric impedence, gastric pH, duodenal peristalsis, duodenal electrical activity, duodenal chemical activity, duodenal hormonal activity, duodenal temperature, duodenal pressure, duodenal impedence, duodenal pH, blood activity, chemical activity, hormonal activity, vagal activity, gastrointestinal neural activity, salivary chemical activity, biliary pressure, biliary electrical activity, biliary chemical activity, pancreatic pressure, pancreatic electrical activity, pancreatic chemical activity, pancreatic sphincter pressure, pancreatic sphincter electrical activity, biliary sphincter pressure, and biliary sphincter electrical activity.

In another embodiment, the present invention is directed to a method for treating obesity in a patient, comprising the steps of: arranging at least one electrode on at least one of a pancreas, a pancreatic duct, a pancreatic sphincter, a bile duct, a cystic duct, a gall bladder, a biliary sphincter, or autonomic nerves supplying the pancreas, and activating said electrode to provide an electrical stimulus thereto, wherein said electrical stimulus is effective to inhibit at least one of fat digestion or fat absorption by the patient or induce satiety in the patient.

In another embodiment, the present invention is directed to a device for electrical stimulation, comprising: a) a pulse generator; and b) at least one electrode set connected to the pulse generator wherein the electrode sets are arranged on at least one of a pancreas, a pancreatic duct, a pancreatic sphincter, a bile duct, a gall bladder, a biliary sphincter, or autonomic nerves supplying the pancreas, such that activating said electrode is effective to modulate secretions of biliary or pancreatic juices.

BRIEF DESCRIPTION OF THE DRAWINGS

These and other objects and advantages of the present invention will become more fully apparent from the following detailed description when read in conjunction with the accompanying drawings with like reference numerals indicating corresponding parts through-out, wherein:

FIG. 2 is a schematic illustration of an exemplary electrode set implanted in the gall bladder;

DETAILED DESCRIPTION OF THE INVENTION

Figure 1:
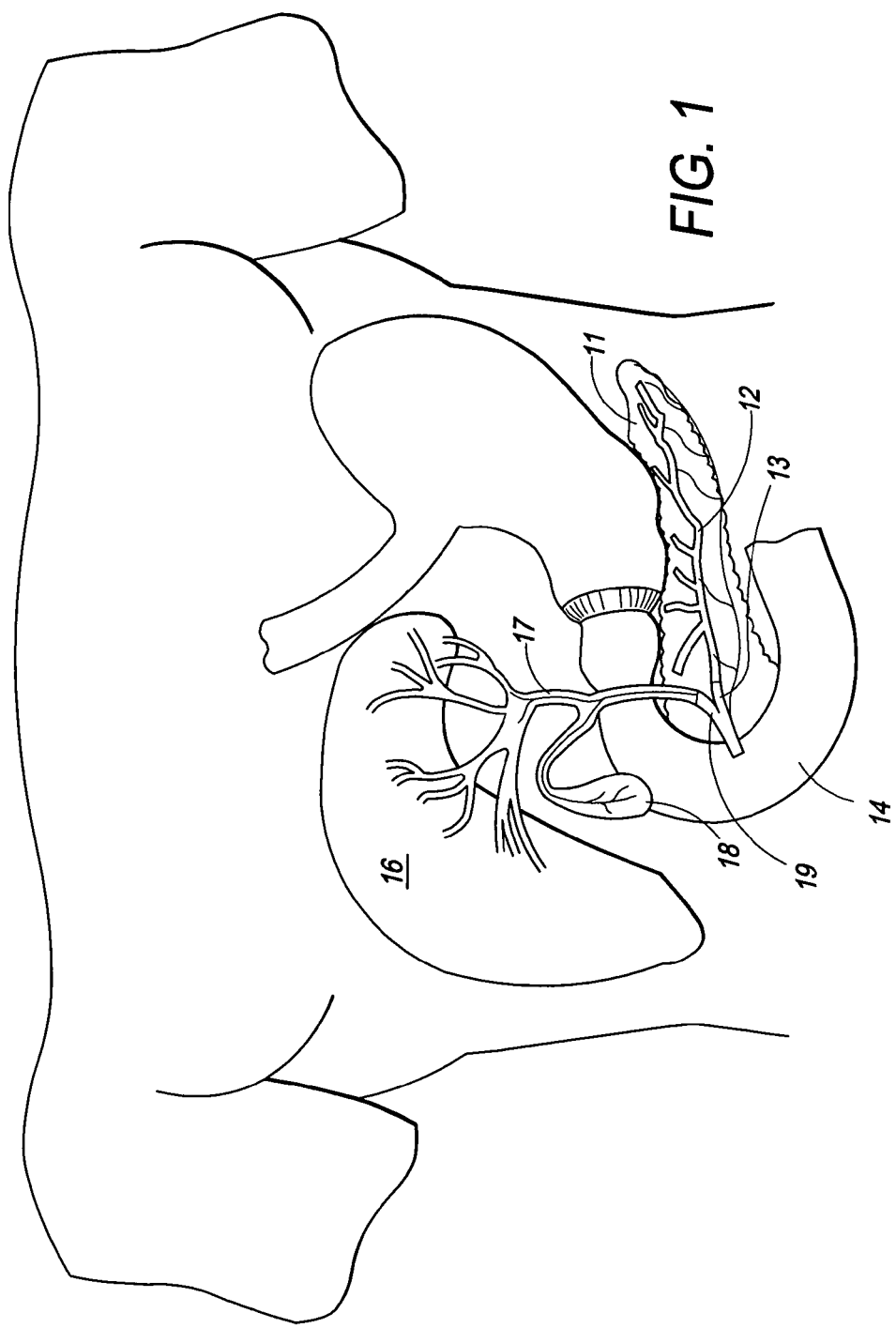
FIG. 1 is a schematic illustration of a portion of the pancreatico-biliary system.

Pancreatico-biliary secretions are important for the digestion of major nutrients and are important components to the digestion of fat. Interruptions in pancreatico-biliary secretions may impair digestion of various nutrients, including fat digestion, and hence will be helpful in management of conditions of over-nutrition including obesity. The present invention is directed toward the novel use of an electrode set and stimulator to treat any one of, or a combination of, the following conditions: pancreatitis, acute pancreatitis, acute biliary pancreatitis, alcoholic pancreatitis, autoimmune pancreatitis, chronic pancreatitis, hemorrhagic pancreatitis, hereditary pancreatitis, idiopathic pancreatitis, necrotizing pancreatitis, post ERCP pancreatitis, tropical pancreatitis, pancreas cancer, acinar cell pancreas cancer, endocrine pancreas cancer, pancreas divisum, pancreas syndrome, pancreas transplant rejection, pancreas transplantation, pancreatic ascites, hereditary pancreas cancer, pancreatic cholera syndrome, pancreatic cysts, pancreatic diabetes, pancreatic diabetes mellitus, pancreatic diabetes mellitus, pancreatic duct disruption, pancreatic duct injury, pancreatic duct obstruction, pancreatic duct stricture, pancreatic fistula, pancreatic exocrine insufficiency, pancreatic endocrine insufficiency, pancreatic insufficiency, pancreatic ischemia, pancreatic mucinous cystadenocarcinoma, pancreatic mucinous cystadenoma, pancreatic mucinous duct ectasia (intraductal papillary mucinous neoplasm), pancreatic pain, pancreatic panniculitis, pancreatic papillary cystic neoplasm, pancreatic pseudocyst, pancreatic serous cystadenoma, pancreatic stones, abnormalities in the pancreaticobiliary junction, Sphincter of Oddi hypertension, Sphincter of Oddi dysfunction, Sphincter of Oddi dyskinesia, gallbladder adenoma, gallbladder adenomyomatosis, gallbladder cancer, gallbladder cholesterol polyps, gallbladder cholesterolosis, gallbladder hypomotility, gallbladder inflammatory polyps, gallbladder lithiasis, gallbladder polyps, gallbladder stasis, asymptomatic gallbladder stones, pigmented gallbladder stones, porcelain gallbladder, strawberry gallbladder, bile acid metabolism disorders, bile acid reflux, bile duct cancer, bile duct leak, bile duct obstruction, common bile duct obstruction, common bile duct stones, bile reflux gastropathy, bile salt induced diarrhea, bile salt malabsorption, cholecystitis, cholecystitis glandularis proliferans, acalculous cholecystitis, acute cholecystitis, chronic cholecystitis, cholecystocholedochal fistula, cholecystocolonic fistula, cholecystoduodenal fistula, cholecystoenteric fistula, cholecystogastric fistula, cholecystohepatic fistula, choledochal cysts (biliary cysts), choledocholithiasis, cholelithiasis, cholestasis caused by citrin deficiency (neonatal intrahepatic), cholestasis of pregnancy (intrahepatic), cholestasis (benign recurrent intrahepatic), cholestasis (extrahepatic, bile duct obstruction), familial intrahepatic cholestasis, functional cholestasis, intrahepatic cholestasis, neonatal cholestasis, progressive familial intrahepatic cholestasis, cholestatic hepatitis, fibrosing cholestatic hepatitis, cholestatic liver disease, cholestatic pruritus, biliary sludge, gallbladder sludge, microlithiasis, obesity, morbid obesity, obesity dyslipidemia syndrome (metabolic syndrome), obesity hypoventilation syndrome, abdominal obesity, hypothalamic obesity, dyslipidemia, familial combined dyslipidemia, dyslipidemia hypertension (insulin resistance, metabolic syndrome), hypercholesterolemia, familial hypercholesterolemia, polygenic hypercholesterolemia, malnutrition, protein calorie malnutrition, vitamin malnutrition, mineral malnutrition, and trace elements malnutrition.

The direct stimulation of pancreas, pancreatic duct or pancreatic sphincter to modulate pancreatic function or exocrine secretion or the stimulation of the biliary system to modulate biliary function or secretions delivers distinct advantages over prior art approaches to stimulating portions of the stomach, vagus nerve or other portions of gastrointestinal tract. First, unlike prior applications of electrical stimulus, the present invention targets the digestive process, in particular the modulation of pancreatic and/or biliary system secretions. When performed, prior art gastrointestinal stimulation, which focused on the esophagus, stomach and vagus, induce a sensation of satiety in a patient, thereby discouraging the patient from ingesting more food. The present application, in contrast, induces both a sensation of satiety in a patient and has the further advantage of inhibiting the absorption of ingested fat by modulating secretions needed to break down and absorb the fat. Once food is ingested, prior art forms of gastrointestinal stimulation can not affect or inhibit the digestion or absorption of the ingested food. Second, the present application targets smaller muscles in the pancreaticobiliary system which can be more readily stimulated, with less electrical amperage, than larger muscles in the gastrointestinal tract. As a result, one can provide a patient with a sense of satiety, and inhibit fat digestion and absorption, with smaller, more targeted electrical stimuli, thereby increasing therapeutic efficacy and improving safety.

Referring now in detail to the various views of the accompanying drawings, FIG. 1 illustrates a portion of the human body comprised of a pancreas 11, a pancreatic duct (PD) 12, a pancreatic sphincter (PS) 13, a liver 16, a bile duct (BD) 17, a gall bladder 18 and a biliary sphincter (BS) 19. The PD 12 and BD 17 are connected to the small intestine 14 via the PS 13 and BS 19, collectively know as the ampullary sphincter, ampula, ampula of Vater or papilla of Vater. The pancreaticobiliary system is supplied by the autonomic nerves 15. The PS and BS act as barriers that control the flow of pancreatic juices from pancreas 11 and bile from BD 17 to small intestine 14. The PS and BS are in tonic contraction but undergo transient periods of relaxation which allow pancreatic and bile juices to flow into the small intestine. If such flow is modulated, a sense of satiety can be induced in a patient and the absorption of fat, which was ingested by the patient, can be inhibited.

In order to reduce pancreatic and bile juices from reaching the small intestine, an electrical stimulus is applied to one or more locations in the PD 12 or PS 13 or the nerves 15 supplying the pancreas, PD or PS or one or more locations in the BD 12 or BS 13 or gallbladder 18 or the nerves supplying the liver, BD, BS or the gallbladder. In particular, the electrical stimulus is preferably applied to at least one of the following: the distal most part of the PD, the distal most part of the BD, the distal most part of the cystic duct, the fundus of the gall bladder, the PS or the BS or the nerves supplying the pancreatico-biliary system. These stimuli cause contraction of at least one or more of the PD, PS, BD, or BS thus preventing the flow of pancreatic or biliary juices into the duodenum and interrupting digestion of nutrients including fat. Stimulation of the gallbladder will increase the flow of the bile into the duodenum thus aiding in digestion, preventing gall bladder stasis and gall bladder sludge or stone formation.

In one embodiment, at least one electrode set is placed near one or more of the pancreas, PD or pancreatic sphincter or liver, BD, BS or the gallbladder. Each electrode set is comprised of at least one active electrode. Alternatively, the electrode set may comprise at least one active electrode and a grounding electrode. The electrode set may be arranged in any pattern that produces the desired stimulation to the BD, BS, PD or PS, such as a circumferential pattern, along a longitudinal axis, irregular, random or other placement. The electrode(s) may also reside in a sleeve that is positioned around the BD, cystic duct, or in the form of a net on the fundus of the gall bladder.

The stimulation of sympathetic autonomic nerves innervating the pancreaticobiliary system will cause a decrease in pancreaticobiliary secretions, relaxation of muscles in the pancreaticobiliary system and cumulatively this will result in lowering of pancreaticobiliary ductal pressures which in turn will prevent or treat disease like biliary colic, pancreatic pain, pancreatitis and sphincter of oddi dysfunction.

FIG. 2 illustrates one embodiment where electrode set 21 is placed in a loose linear configuration in the gallbladder 18 of a patient with gallbladder disease such as cholecystitis, cholelithiasis or gall bladder sludge. A device 26, comprising a pulse generator or microcontroller, transmits a signal that causes the electrode set to deliver an electrical stimulation to the gallbladder. The device 26 is connected to a power source 28 for supplying a source of power. The device 26 is further connected to the electrode set 21 by wires 20 for transmitting an electrical stimulus signal to the electrode set 21. Alternatively, the electrode set 21 may be coupled to the pulse generator 26 in a wireless fashion using an RF link, an ultrasonic link, a thermal link, a magnetic, an electromagnetic or an optical link. The stimulating electrode 21 can stimulate the gall bladder 18 to induce emptying of the bile from gall bladder into the duodenum 14. This will prevent gall bladder stasis and gallstone or sludge formation. Stimulation can be performed at pre-programmed intervals, pursuant to a pre-defined protocol, or at regular intervals to promote emptying, prevent gall bladder stasis and gall bladder diseases associated with bile stasis such as cholecystitis, gall stones and gall bladder cancer.

Alternatively, a set of sensing electrodes can detect one of the physiological parameters associated with passage of nutrients from stomach into the duodenum and generate a signal to cause the delivery of an electrical stimulus which would result in meal induced emptying of the bile from gall bladder into the duodenum 14. This will also prevent gall bladder stasis and gallstone or sludge formation. The physiological stimuli can include any one of the following: changes in gastric or duodenal pH, changes in gastric, duodenal or pancreaticobiliary electrical activity from fasting to fed pattern, changes in gastric, duodenal or pancreaticobailiary impedance associated with eating, changes in gastric, duodenal or pancreaticobiliary peristaltic activity as measured by pressure, stretch or directionality by impedance, changes in luminal content measured by chemical analysis, or eating-induced changes in intraluminal temperature in the stomach or duodenum. Such sensing of various physiological stimuli can be performed in any number of ways known to persons of ordinary skill in the art, including placing one or more electrical sensors in the wall of the gall bladder to measure intrinsic gall bladder electrical activity, placing one or more pressure sensors in the gall bladder lumen to measure gall bladder pressure or impedance or placing one or more chemical sensors in the duodenum to sense arrival for food from the stomach. It should be appreciated that all sensors can be connected in a wired or wireless fashion to the microcontroller.

EXAMPLE ONE

In one exemplary application, a forty-five year old female complains of right upper quadrant pain for the last 6 months. The pain is exacerbated by meals, mainly fatty meals. She has a family history of gall bladder cancer. An ultrasound reveals that she has gall bladder sludge. A HIDA scan (cholescintigraphy) showed poor gall bladder ejection fraction.

To alleviate those symptoms and reduce gall bladder sludge, the patient undergoes the laproscopic implantation of a gall bladder stimulator. The stimulator leads are implanted in the fundus of gall bladder and the microcontroller is implanted in a pocket in the anterior abdominal wall. An external microcontroller could have been used instead and worn on the patient's belt, together with a charger that charges the microstimulator via RF signaling.

To active the stimulator, the patient uses a remote control that signals to the microcontroller when the patient ingests a meal. Based on patient's gastric emptying time, the microcontroller sends multiple trains of pulses, starting at the beginning of gastric emptying and finishing at the end of the gastric emptying time. Typical stimulation parameters can have a pulse amplitude of 20 mAmp and a pulse frequency of 20 pulses per second. The pulse trains are interrupted by a quiescent phase of 10 seconds to allow for repolarization of the gall bladder muscle. The pulse trains stimulate contraction of the gall bladder resulting in meal induced emptying of the gall-bladder. This will prevent gall bladder stasis and gallstone formation. Prevention of stasis will also help prevent gall bladder cancer.

Figure 2A:
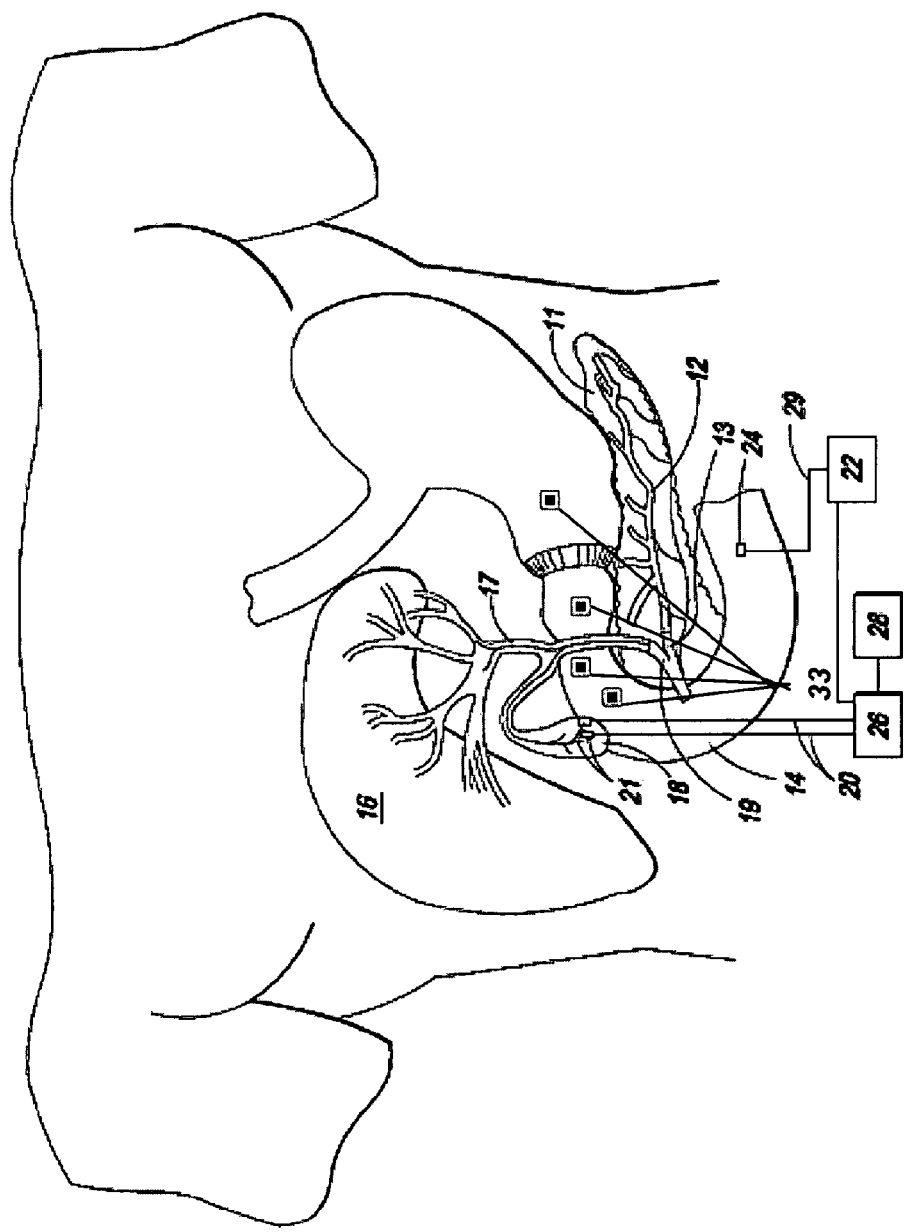
FIG. 2A is a schematic illustration of an exemplary implanted impedence sensor set for the measurement of impedence.

Alternatively, referring to FIG. 2A, the patient could also have implanted one or more impedance sensors 33 in the duodenal bulb that sense entry of chime from the stomach into the duodenum and trigger the microcontroller 26 which, in turn, triggers the electrode set 21 to deliver the stimulations to the gall bladder. The impedance sensors 33 will also detect end of chime flow from the stomach into the duodenum and send a shut off signal to the microcontroller 26 which, in turn, shuts off the microstimulator.

Figure 2B:
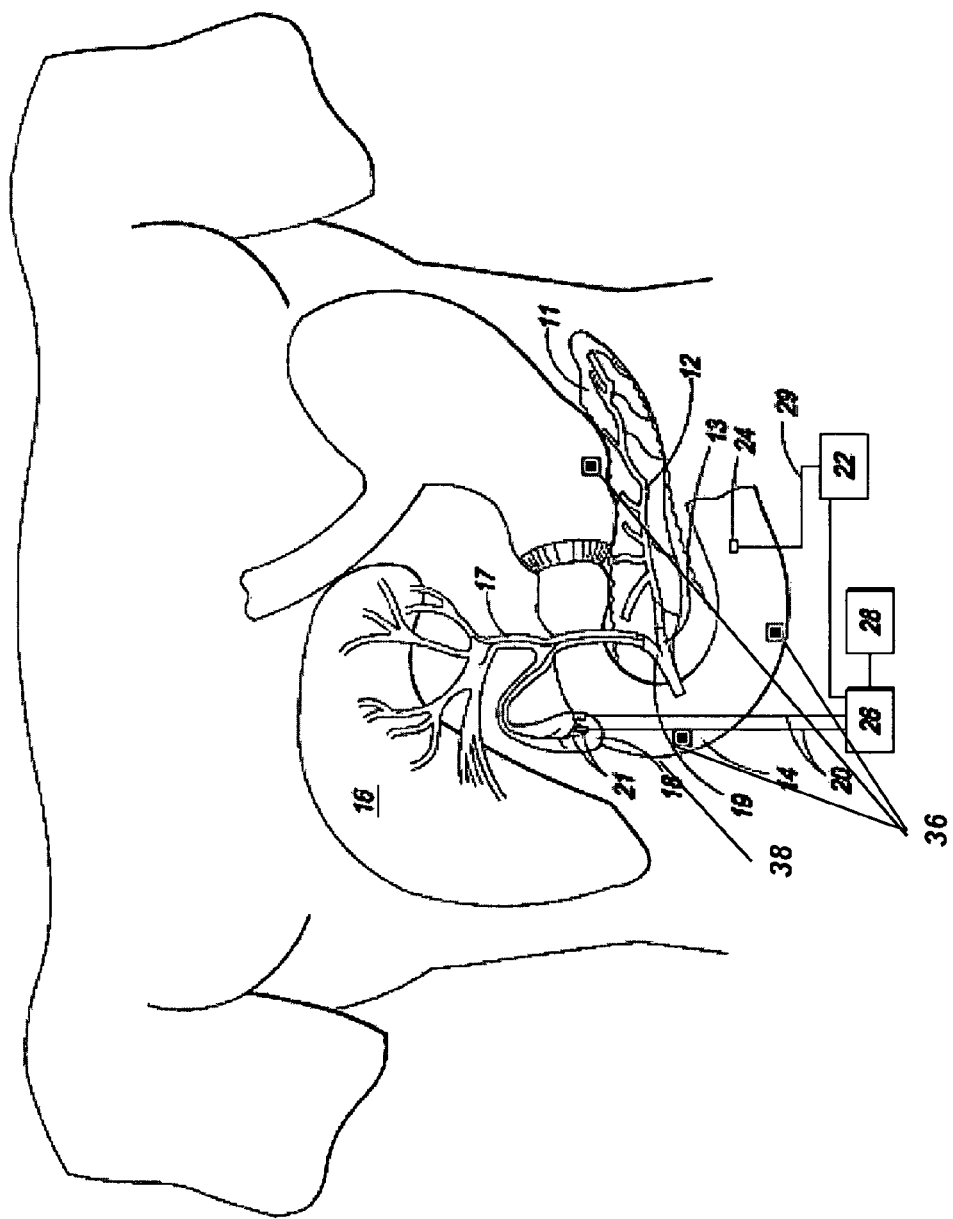
FIG. 2B is a schematic illustration of an exemplary implanted electrical sensor set that sense changes in a patient's duodenal electrical pattern.

Alternatively, referring to FIG. 2b, the patient could also have implanted electrical sensors 36 in the duodenal wall 38 that sense change in the duodenal electrical pattern from fasting to fed phase upon entry of chime from the stomach into the duodenum. This will trigger the microcontroller 26 and to deliver stimulation via the electrode set 21 to the gall bladder. The end of chime flow will cause the duodenal electrical activity pattern to change from fed to fasting state which, in turn, will shut off the microcontroller 26. Based on the degree of gall bladder dysfunction, additional timed stimulation at regular intervals can be schedule to facilitate gall bladder emptying and prevent bile stasis, gall stone formation and gall bladder cancer.

Figure 3:
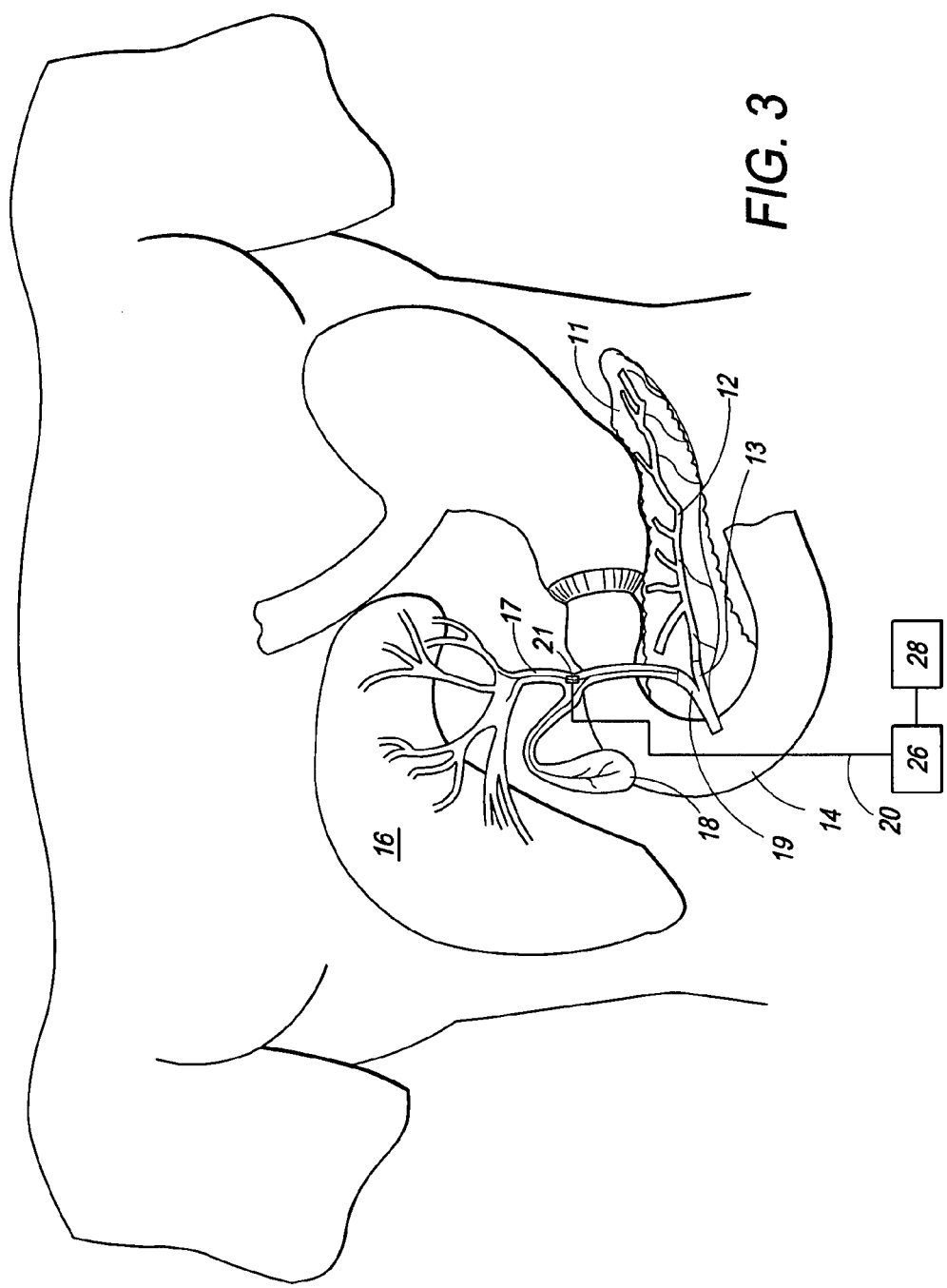
FIG. 3 is a schematic illustration of an exemplary electrode set implanted in the bile duct.

FIG. 3 shows another embodiment in which the electrode set 21 is placed in the BD 17, including the cystic duct, of a patient suffering from eating disorders such as overweight, obesity or cholesterol disorder. The device comprising a pulse generator or microcontroller 26 is connected to a power source 28 for supplying a source of power. The device 26 is further connected to the electrode set 21 by wires 20, as previously described. Alternatively, the electrode set 21 may be coupled to the device 26 in a wireless fashion. The stimulating electrode 21 can stimulate the bile duct 18 to prevent emptying of the bile from gall bladder and liver into the duodenum 14 by causing contraction of the bile duct or a part of the bile duct. The stimulus can be timed at a pre-specified time from initiation of eating. The pre-specified time is dependent on amount of caloric intake recommended or amount of weight loss desired. This will induce symptom of fullness and satiety and curb a patient's appetite. Alternatively, a set of sensing electrodes can detect one of the physiological parameters associated with a meal and generate a signal to cause the delivery of an electrical stimulus which would prevent emptying of the bile from gall bladder and liver into the duodenum 14. This will once again induce symptom of fullness and satiety and curb once appetite. In addition, interrupting the secretion of bile in to the duodenum at the time of a meal will induce fat malabsorption and result in further weight loss.

In one embodiment, a health care provider programs the timing of the stimulus. One of ordinary skill in the art would appreciate that the pulse generator can be in data communication with a programmable memory, EEPROM, or other programmable chip device that can be programmed to cause the pulse generator to generate a stimulus in accordance with a pre-defined schedule. By appropriately defining the timing of the stimulus, one can determine how much caloric intake is allowed by the patient. For example, in a patient that requires moderate amount of weight loss and moderate caloric restriction the pre-specified stimulus time can be 10 minutes. This will allow patient 10 minutes to eat his meal following which satiety is induced via stimulation and patient will stop eating.

In contrast, in a patient that requires a severe amount of weight loss and severe caloric restriction, the pre-specified time can be 5 minutes. This will allow patient 5 minutes to eat his meal following which satiety is induced via stimulation and patient will stop eating. Alternatively, the patient can manually trigger the stimulus upon feeling hunger, food cravings, or a desire to eat.

EXAMPLE TWO

In a second exemplary application, a thirty five year old male weighing 412 lbs, with a body mass index of 42, is referred to a surgeon for a bariatric procedure. The patient suffers from insulin dependent diabetes mellitus, moderate hypertension, obstructive sleep apnea and high cholesterol. The patient undergoes a laparoscopic implantation of the bile duct stimulator. The stimulator leads are implanted on the serosal surface of the distal bile duct and the microcontroller is implanted in a pocket in the anterior abdominal wall. Alternatively, the microstimulator could have been laproscopically or endoscopically implanted in the distal bile duct with the external microcontroller worn on the patient's belt to charge the microstimulator via RF signaling.

Using remote control signals, the patient signals the ingestion of a meal. Based on patient's desired weight loss, the microcontroller sends multiple trains of pulses after a preset time delay. In this particular patient, a 150 lb weight loss is desired and a 1000 calorie daily diet is suggested. Consequently, the preset time to start biliary stimulation is determined to be 10 minutes from the initiation of eating. A typical stimulation parameter can have a pulse amplitude of 10 mAmp and a pulse frequency of 30 pulses per second. The pulse trains are interrupted by a quiescent phase of 30 seconds to allow for repolarization of the bile duct muscle. The pulse trains will induce contraction of the bile duct resulting in physiological obstruction to the flow of bile. This will cause increased pressure in the bile duct, biliary system distension and initiate a sensation of satiety or loss of appetite in the patient.

Alternatively, electrodes can be implanted in the distal bile duct and a reverse stimulation sequence, using the same stimulation parameters, may be applied, thereby resulting in a physiological obstruction to the bile flow which, in turn, induces satiety or loss of appetite. The stimulation is carried out until all the chime passes the duodenum, after which the stimulation stops. The biliary secretions are then released into the small intestine, resulting in the dissociation between biliary secretion and the passage of food through the intestinal lumen and thereby disrupting digestion and absorption of fat causing further weight loss and lowering of cholesterol.

Alternatively, impedance sensors can be implanted in the duodenal bulb that sense the entry of chime from the stomach into the duodenum and trigger the microcontroller which, in turn, triggers the stimulator to deliver stimulations to the bile duct. The impedance sensors will also detect end of chime flow from the stomach into the duodenum and transmit a shut off signal to the microcontroller which, in turn, will shut off the stimulator.

Alternatively, electrical sensors can be implanted in the gastric or duodenal wall that sense change in the electrical pattern which signals a change from fasting to fed phase upon entry of food into the stomach or the duodenum. This will trigger the microcontroller and the stimulator to deliver stimulation to the bile duct. The end of chime flow will turn the duodenal electrical activity pattern from fed to fasting state which, in turn, will shut off the microcontroller and the bile duct stimulator. Based on patients continuing caloric restriction the stimulation patterns could be adjusted by the patient's physician using an external remote controller without necessitating additional surgery. Upon achieving desired weight loss, the stimulator could be remotely shut down and, if the patient starts gaining the weight back, the stimulator could be remotely turned on.

Figure 4:
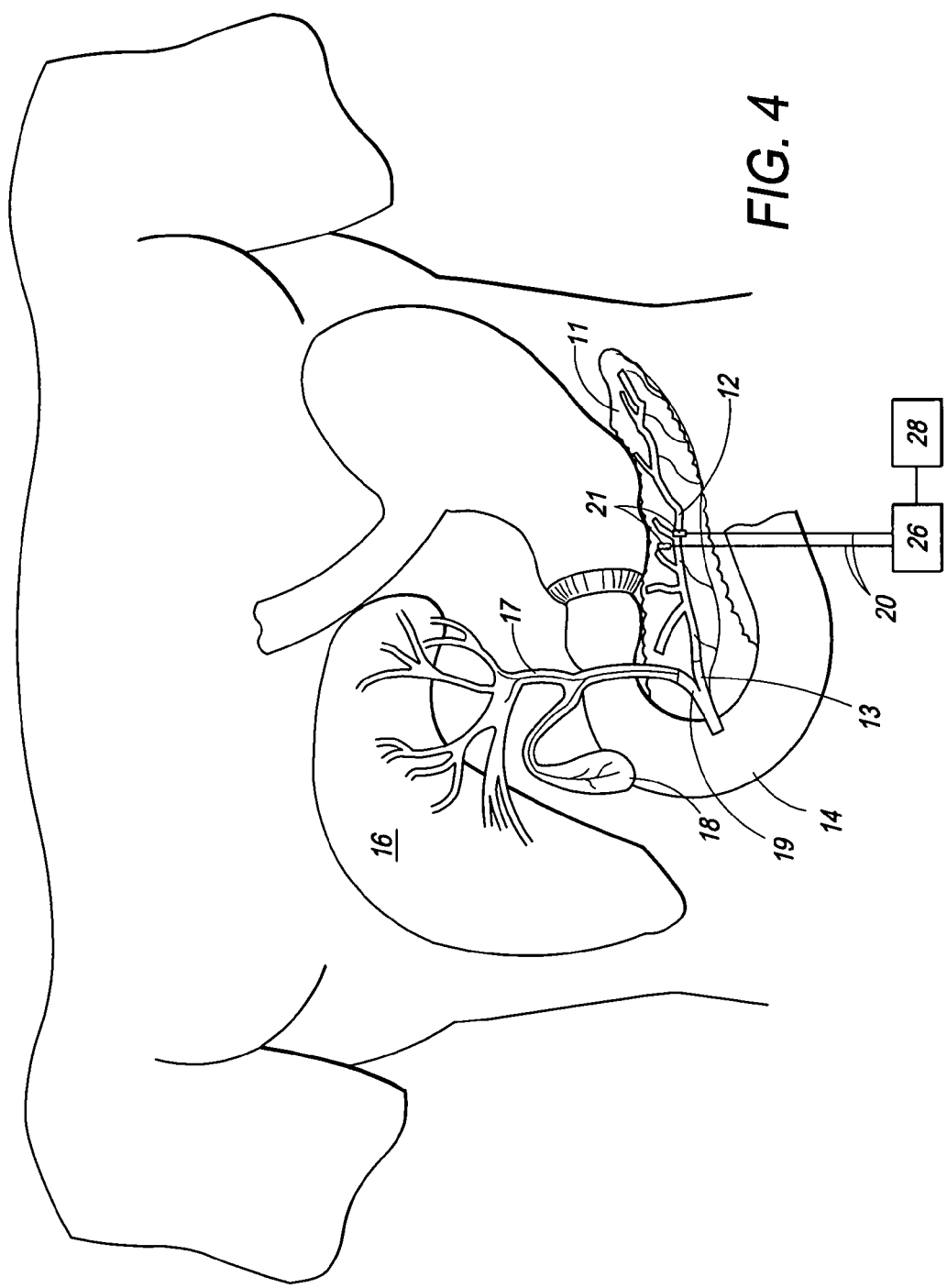
FIG. 4 is a schematic illustration of an exemplary electrode set implanted in the pancreatic duct.

FIG. 4 shows another embodiment in which the electrode set 21 is placed in the pancreas 11 or PD 12, also in a loose linear configuration, in a patient with eating disorders such as overweight, obesity or cholesterol disorder. The device comprising a pulse generator 26 is connected to a power source 28 for supplying a source of power. The device is further connected to the electrode set 21 by wires 20, as previously described. Alternatively, the electrode set 21 may be coupled to the device 26 in a wireless fashion. The stimulating electrode 21 can stimulate the pancreatic duct 12 to prevent emptying of the pancreatic juices from the pancreas into the duodenum 14. The stimulus can be timed at a pre-specified time from initiation of eating. The pre-specified time is dependent on amount of caloric intake recommended or amount of weight loss desired. This will induce symptom of fullness and satiety and curb a patient's appetite. Alternatively, a set of sensing electrodes can detect one of the physiological parameters associated with a meal and generate a signal to cause the delivery of an electrical stimulus which would prevent emptying of the pancreatic juices from pancreatic duct 12 into the duodenum 14. This will once again induce symptom of fullness and satiety and curb once appetite.

In one embodiment, a health care provider programs the timing of the stimulus. One of ordinary skill in the art would appreciate that the pulse generator can be in data communication with a programmable memory, EEPROM, or other programmable chip device that can be programmed to cause the pulse generator to generate a stimulus in accordance with a pre-defined schedule. By appropriately defining the timing of the stimulus, one can determine how much caloric intake is allowed by the patient. For example, in a patient that requires moderate amount of weight loss and moderate caloric restriction the pre-specified stimulus time can be 10 minutes. This will allow patient 10 minutes to eat his meal following which satiety is induced via stimulation and patient will stop eating. In contrast, in a patient that requires a severe amount of weight loss and severe caloric restriction, the pre-specified time can be 5 minutes. This will allow patient 5 minutes to eat his meal following which satiety is induced via stimulation and patient will stop eating. Alternatively, the patient can manually trigger the stimulus upon feeling hunger, food cravings, or a desire to eat. This will once again induce symptom of fullness and satiety and curb once appetite. Pancreatic enzyme secretion from the pancreas is essential for fat absorption. Interrupting secretion of pancreatic enzyme in to the duodenum at the time of meal will induce fat malabsorption and result in further weight loss and lowering of patient's cholesterol.

EXAMPLE THREE

In a third exemplary application, a fifty five year old female weighing 265 lbs, with a body mass index of 35, is referred to a surgeon for a bariatric procedure. The patient suffers from insulin dependent diabetes mellitus, moderate hypertension, obstructive sleep apnea, degenerative joint disease, reflux disease uncontrolled by medications, and high cholesterol. The patient undergoes a laparoscopic implantation of the pancreatic duct stimulator. The stimulator leads are implanted on the serosal surface of the distal pancreatic duct and the microcontroller is implanted in a pocket in the anterior abdominal wall. Alternatively, a microstimulator could have been laproscopically or endoscopically implanted in the distal pancreatic duct with the external microcontroller placed on the patient's belt to charge the microstimulator via RF signaling.

Using the remote control, the patient signals the ingestion of a meal. Based on patient's desired weight loss, the microcontroller transmits multiple trains of pulses after a preset time delay. In this particular patient, a 100 lb weight loss is desired and a 1200 calorie daily diet is suggested. Consequently, the preset time to start pancreatic stimulation is determined to be 15 minutes from the initiation of eating. A typical stimulation parameter can have a pulse amplitude of 10 mAmp and a pulse frequency of 10 pulses per second for a duration of 5 seconds. The pulse trains are interrupted by a quiescent phase of 30 seconds to allow for repolarization of the pancreatic duct muscle. The pulse trains induce contraction of the pancreatic duct resulting in physiological obstruction to the flow of the pancreatic juices. This will cause increased pressure in the pancreatic duct and pancreatic ductal system distension, and will initiate a sensation of satiety or loss of appetite in the patient.

Alternatively, electrodes can be implanted in the distal pancreatic duct and used to generate a reverse stimulation sequence under the same stimulation parameters, thereby creating a physiological obstruction to the pancreatic juice flow which, in turn, induces satiety or loss of appetite. The stimulation is carried out until all the chime passes the duodenum, after which the stimulation stops. The pancreatic secretions are then released into the small intestine which result in dissociation between pancreatic secretions and the passage of food through the intestinal lumen. This will disrupt enzymatic digestion of both proteins and fat, resulting in further weight loss and lowering of cholesterol.

Alternatively, impedance sensors can be implanted in the duodenal bulb that sense the entry of chime from the stomach into the duodenum and trigger the microcontroller which, in turn, triggers the stimulator to deliver stimulations to the pancreatic duct. The impedance sensors also detect the end of chime flow from the stomach into the duodenum and transmits a shut off signal to the microcontroller which, in turn, will shut off the microstimulator.

Alternatively, electrical sensors can be implanted in the gastric or duodenal wall to sense change in electrical patterns signaling a change from a fasting to a fed state upon entry of food into the stomach or the duodenum. This will trigger the microcontroller and the stimulator to deliver stimulation to the pancreatic duct. The end of chime flow will turn the duodenal electrical activity pattern from fed to fasting state, which, in turn, will shut off the microcontroller and the pancreatic duct stimulator. Based on patient's continuing caloric restriction, the stimulation patterns could be adjusted by the patient's physician using an external remote controller without necessitating additional surgery. Upon achieving desired weight loss the stimulator could be remotely shut down and, if the patient starts gaining the weight back, the stimulator could be remotely turned on.

Figure 5:
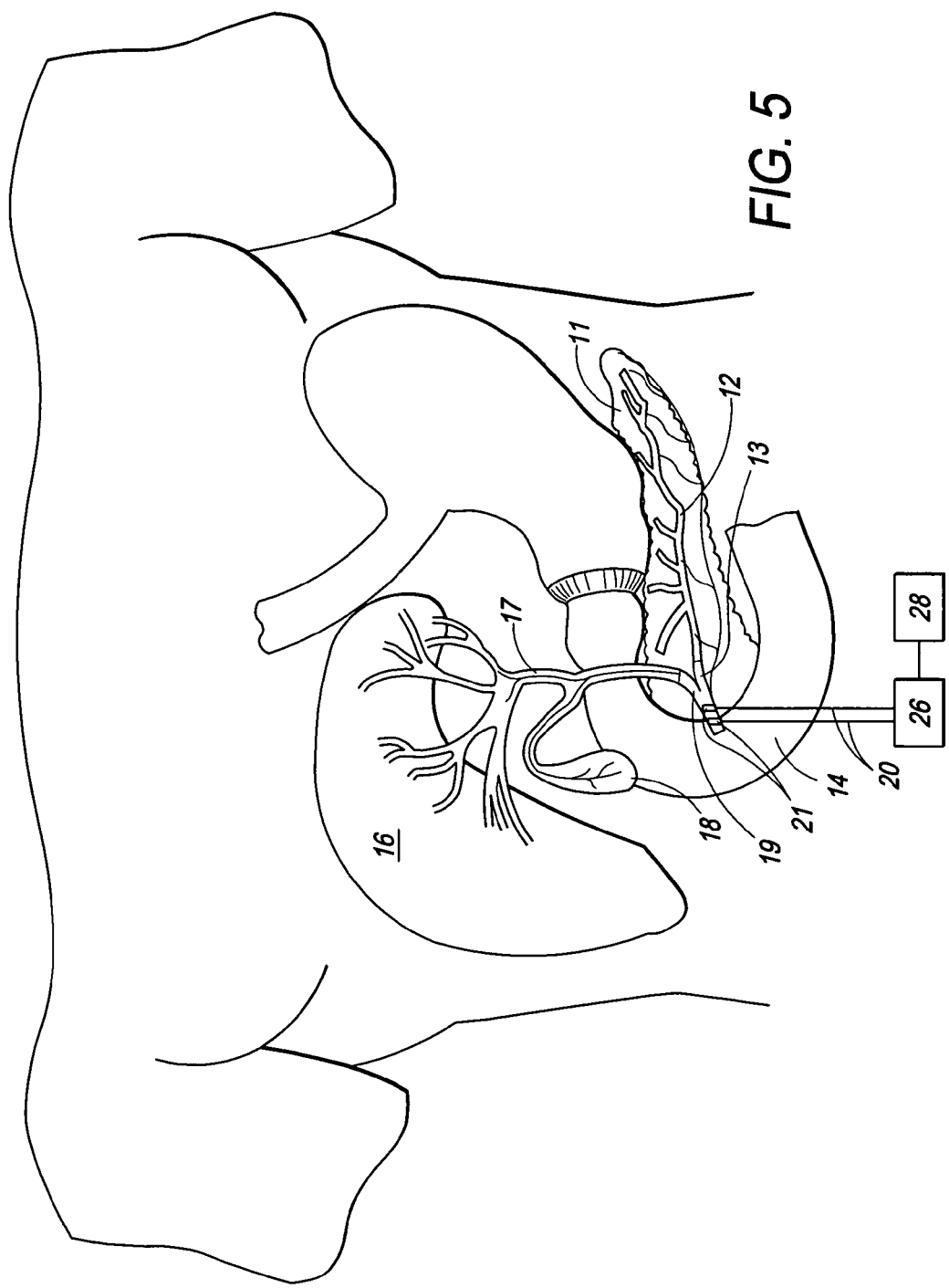
FIG. 5 is a schematic illustration of an exemplary electrode set implanted in the ampullary sphincter.

FIG. 5 shows another embodiment in which the electrode set 21 is placed in the PS 13, BS 19 or both, also in a loose linear configuration, in a patient with eating disorders such as overweight, obesity or cholesterol disorder. The device comprising a pulse generator 26 is connected to a power source 28 for supplying a source of power. The device 26 is further connected to the electrode set 21 by wires 20, as previously described. Alternatively, the electrode set 21 may be coupled to the device 26 in a wireless fashion. The stimulating electrode 21 can stimulate the PS 13, BS 19 or both to prevent emptying of the bile and pancreatic juices into the duodenum 14. The stimulus can be timed at a pre-specified time from initiation of eating. The pre-specified time is dependent on amount of caloric intake recommended or amount of weight loss desired. This will induce symptom of fullness and satiety and curb a patient's appetite. Alternatively, a set of sensing electrodes can detect one of the physiological parameters associated with a meal and generate a signal to cause the delivery of an electrical stimulus which would prevent emptying of the bile and pancreatic juices into the duodenum 14. This will once again induce symptom of fullness and satiety and curb once appetite.

In one embodiment, a health care provider programs the timing of the stimulus. One of ordinary skill in the art would appreciate that the pulse generator can be in data communication with a programmable memory, EEPROM, or other programmable chip device that can be programmed to cause the pulse generator to generate a stimulus in accordance with a pre-defined schedule. By appropriately defining the timing of the stimulus, one can determine how much caloric intake is allowed by the patient. For example, in a patient that requires moderate amount of weight loss and moderate caloric restriction the pre-specified stimulus time can be 10 minutes. This will allow patient 10 minutes to eat his meal following which satiety is induced via stimulation and patient will stop eating. In contrast, in a patient that requires a severe amount of weight loss and severe caloric restriction, the pre-specified time can be 5 minutes. This will allow patient 5 minutes to eat his meal following which satiety is induced via stimulation and patient will stop eating. Alternatively, the patient can manually trigger the stimulus upon feeling hunger, food cravings, or a desire to eat. This will once again induce symptom of fullness and satiety and curb once appetite. In addition, preventing the secretion of bile and pancreatic juices at the time of a meal will induce both nutrient and fat malabsorption and result in further weight loss.

EXAMPLE FOUR

In a fourth exemplary application, a forty five year old male weighing 305 lbs, with a body mass index of 35, is referred to a surgeon for a bariatric procedure. The patient suffers from insulin dependent diabetes mellitus, moderate hypertension, obstructive sleep apnea, degenerative joint disease, reflux disease uncontrolled by medications, high cholesterol, coronary disease with a recent myocardial infarction, and three prior coronary stent placements. Patient continues to have exertional angina and weight reduction is recommended. Because of his significant coronary disease, the patient is deemed a high risk candidate for a roux-en-y gastric bypass surgery. Stimulator implantation is recommended instead.

The patient undergoes a laparoscopic implantation of the ampullary sphincter stimulator. The stimulator leads are implanted into the ampullary sphincter, and the microcontroller is implanted in a pocket in the anterior abdominal wall. Alternatively, a microstimulator could be laproscopically or endoscopically implanted into the ampullary sphincter with the external microcontroller being worn on the patient's belt to charge the microstimulator via RF signaling.

Using a remote control, the patient signals the ingestion of a meal. Based on the patient's desired weight loss, the microcontroller sends multiple trains of pulses after a preset time delay. In this particular patient, a 150 lb weight loss is desired and a 1000 calorie daily diet is suggested. Consequently, the preset time to start pancreatic stimulation is determined to be 10 minutes from the initiation of eating. A typical stimulation parameter can have a pulse amplitude of 10 mamp and a pulse frequency of 10 pulses per second. The pulse trains are interrupted by a quiescent phase of 30 seconds to allow for repolarization of the ampullary sphincter muscle. The pulse trains will induce contraction of the ampullary sphincter resulting in a physiological obstruction to the flow of both biliary and pancreatic juices. This will cause increased pressure in both the pancreatic and biliary sphincters and will cause pancreatic and biliary ductal system distension. This will also initiate a sensation of satiety or loss of appetite in the patient. The stimulation is carried out till all the chime passes the duodenum following which the stimulation stops. The pancreatic and biliary secretions are then released into the small intestine, resulting in the dissociation between the pancreatic and biliary secretions and the passage of food through the intestinal lumen and disrupting enzymatic digestion of both proteins and fat, thereby causing weight loss and lowering of cholesterol.

Alternatively, impedance sensors can be implanted in the duodenal bulb that sense the entry of chime from the stomach into the duodenum and trigger the microcontroller which, in turn, triggers the stimulator to deliver stimulations to the ampullary sphincter. The impedance sensors will also detect end of chime flow from the stomach into the duodenum and transmit a shut off signal to the microcontroller which, in turn, will shut off the microstimulator.

Alternatively, electrical sensors can be implanted in the gastric or duodenal wall that sense changes in electrical patterns signaling a change from a fasting to fed state upon entry of food into the stomach or the duodenum. This will trigger the microcontroller and the stimulator to deliver stimulation to the ampullary sphincter. The end of chime flow will turn the duodenal electrical activity pattern from a fed to fasting state which, in turn, will shut off the microcontroller and the ampullary sphincter stimulator. Based on the patient's continuing caloric restriction, the stimulation patterns could be adjusted by the patient's physician using an external remote controller without necessitating additional surgery. Upon achieving desired weight loss, the stimulator could be remotely shut down and, if the patient starts gaining the weight back, the stimulator could be remotely turned on.

Figure 6:
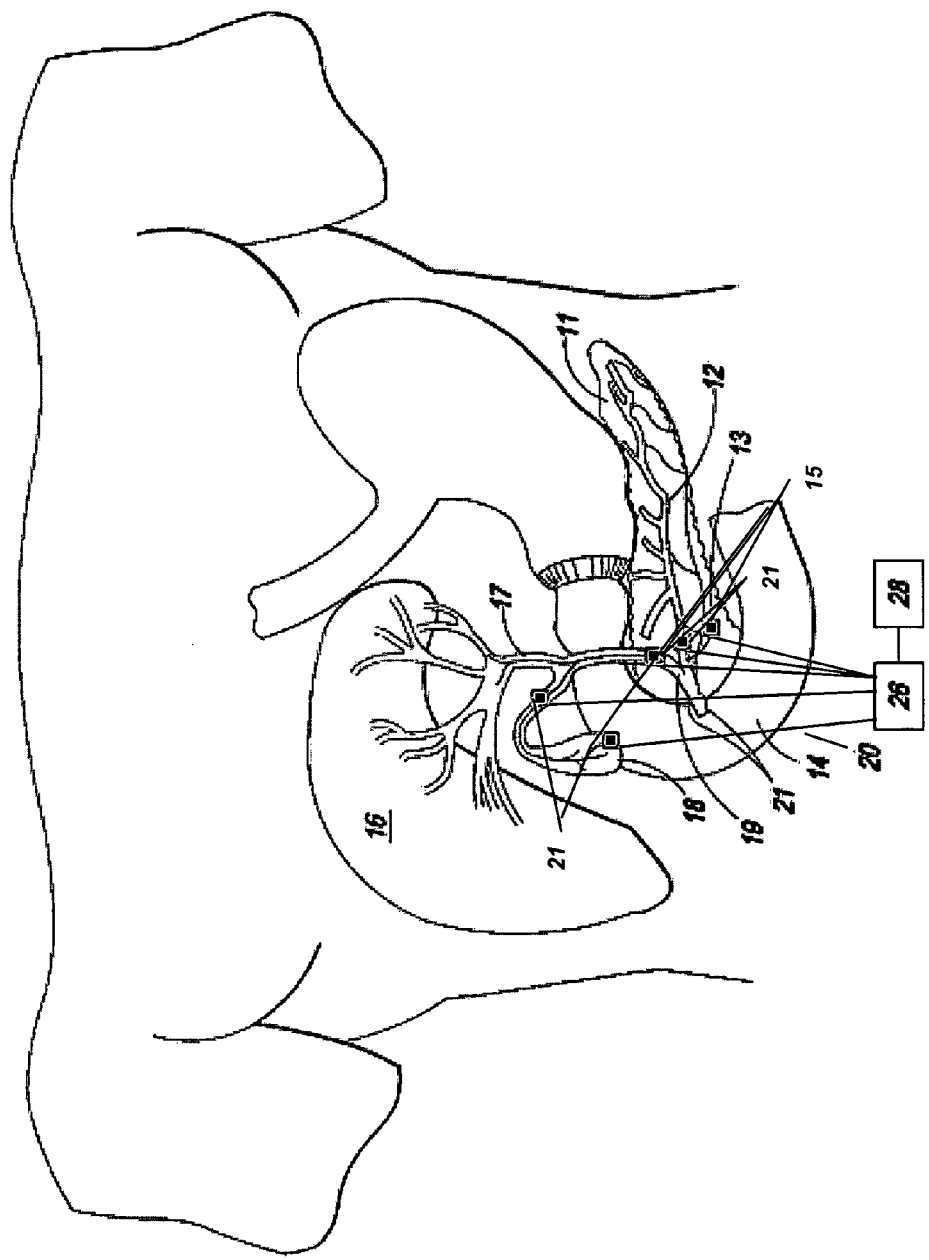
FIG. 6 is a schematic illustration of an exemplary electrode set implanted in the nerves innervating the pancreaticobiliary system.

FIG. 6 shows another embodiment in which a plurality of electrode sets 21 are placed around at least the sympathetic autonomic nerves stimulating the pancreas and biliary system 15, also in a loose linear configuration in a patient with pancreatic pain or recurrent pancreatitis and in areas of the cystic duct, gall bladder, bile duct and pancreatic duct. The device comprising a pulse generator or microcontroller 26 is connected to a power source 28 for supplying a source of power. The pulse generator is further connected to the electrode sets 21 by wires 20 for applying the electrical stimulus to the electrode sets 21 as previously described. Alternatively, the electrode sets 21 may be coupled to the pulse generator 26 in a wireless fashion. The stimulating electrode 21 can stimulate the sympathetic autonomic nerves supplying the pancreas to prevent pancreatic enzyme secretion and relaxation of PD and PS. The stimulus can be continuous or intermittent or timed at a pre-specified time from initiation of eating. The stimulation of the sympathetic autonomic nerves will result in pancreatic rest and decrease pressure in the pancreatic system which, in turn, will decrease pancreatic pain and pancreatitis.

EXAMPLE FIVE

In a fifth exemplary application, a thirty six year old female has chronic abdominal pain and bouts of chronic relapsing pancreatitis. An extensive work-up revealed no etiology for her pancreatitis. A CCK-HIDA scan replicated the pain, raising the suspicion of pancreatitis due to sphincter of oddi/pancreatic ductal hypertension. The patient refused to undergo an ERCP due to the 30% risk of pancreatitis from ERCP in this situation. A decision to proceed with a pancreatic stimulator was made. The stimulator leads were laproscopically implanted around the sympathetic autonomic nerves supplying the pancreas. The pancreatic sympathetic autonomic nerves were stimulated at a continuous rate of 5 cycles per second at 10 mAmp. The stimulation of sympathetic autonomic nerves resulted in a decrease in pancreatic secretions, a decrease in pancreatic sphincter and ductal pressure which, in turn, results in pancreatic rest, a decrease pancreatic pain and a decreased risk of pancreatitis.

In each embodiment, the electrode set provides an electrical stimulus of less than 10 amp and preferably less than 1 amp with most likely therapeutic range of 1-50 mAmp. The electrical stimulus can be provided continuously or intermittently, for example one time or more per hour. Over time, stimulation, whether continuous or intermittent, may serve to tone the smooth muscle of the pancreatico-biliary system. With sufficient tone, further electrical stimulation may be reduced or avoided. Pancreatico-biliary diseases may be successfully treated with a single treatment, or life-long stimulation may be required.

The electrical stimulus may have any shape necessary to produce the desired result, including a square, rectangular, sinusoidal, or sawtooth shape. The frequency of the electrical stimulus is in the range of approximately 1 mHz to 1 MHz. The stimulus may be triggered by a transmitter (not shown) external to the human body, similar to a remote transmitter for a cardiac pacemaker. With appropriate power settings and treatment periods, pancreatico-biliary diseases are eliminated without causing permanent injury to the surrounding tissue or organs. The electrode set 21, can be placed in the mucosal, submucosal, muscularis or serosal layer of the GB 18, BD 17, PD 12, PS 13 or BS 19.

The electrode set is powered by a device 26 comprising a pulse generator or microcontroller that transmits an electrical signal to the electrode set. Alternatively, the electrode set 21 may be coupled to the device 26 in a wireless fashion. The power source 28 can be either a direct current source or an alternating current source. The number of electrode sets is determined by a number of factors, including the size of the electrodes, their power, and the size of the desired placement area. Preferably, the device 26 is controlled by a microprocessor 22 for applying an electrical stimulus for periods of varying duration and varying power/frequency so as to produce the desired contractions.

In an exemplary embodiment, the methods of the present invention are achieved using a neurostimulation system having at least one electrode set, at least one power source, and an extension connecting the power source to the electrode set. The electrode can be integrated into a lead, where the lead is a small conductor with more than one electrode integrated therein. In one embodiment, surgically implanted leads from Medtronic are used, including, but not limited to, the 3587A Resume II Lead, 3986 Resume TL Lead, 3998 Specify Lead, 3999 Hinged Specify Lead, or 3982 SymMix Lead, 3987 On-Point PNS Lead, or any other quadripolar leads with plate electrodes to create multiple stimulation combinations and a broad area of paresthesia.

In one embodiment, the power source which provides electrical pulses for stimulation, also referred to as device 26 in the figures is an implantable battery-powered neurostimulator (or "battery") with non-invasive programmability, such as Itrel 3™, Synergy™, SynergyPlus$^{+}$™, or SynergyCompact$^{-}$™ from Medtronic™. Alternatively, the device comprises a radio-frequency (RF) system, which includes an implanted receiver that detects radio-frequency signals through the skin from an external power source or transmitter, such as Mattrix™ transmitters available from Medtronic™.

In another embodiment, the extension is a small conductor that electrically connects the power source to the lead. Exemplary extensions include a low profile, low impedance extensions and bifurcated, low profile and low impedance extensions.

As shown in FIG. 2 and discussed in the embodiments above, the present invention can optionally include additional sensing electrodes 24 that are placed in the gastrointestinal tract, or proximate to nerves supplying the gastrointestinal tract or the vascular system, to sense physiological stimuli. The physiological stimuli is one or more of esophageal peristalsis, esophageal pH, esophageal impedance, esophageal pressure, esophageal electrical activity, LES pressure, LES electrical activity, gastric peristalsis, gastric electrical activity, gastric chemical activity, gastric hormonal activity, gastric temperature, gastric pressure, gastric impedance and gastric pH, duodenal peristalsis, duodenal electrical activity, duodenal chemical activity, duodenal hormonal activity, duodenal temperature, duodenal pressure, duodenal impedence and duodenal pH, blood chemical and/or hormonal activity, vagal or other gastrointestinal neural activity and salivary chemical activity, biliary pressure, biliary electrical activity, biliary chemical activity, pancreatic pressure, pancreatic electrical activity, pancreatic chemical activity, pancreatic sphincter pressure, pancreatic sphincter electrical activity, biliary sphincter pressure, or biliary sphincter electrical activity.

Upon sensing appropriate physiological stimuli, the sensing electrodes 24 transmit a signal to the device 26, via wire or lead 29 and processor 22, which, based upon the signal received from the sensing electrodes, stops, starts, or otherwise modifies the electrical stimulation signal sent to the electrode set 21. By doing so, the present invention can be more reactive to a patient's particular biological state and precisely modulate the pancreatico-biliary system so that a part or the whole of the pancreatico-biliary system can contract or relax and the flow of pancreatic-biliary juices into the small intestine can be controlled. Control of the pancreaticobiliary system can also be achieved by turning off the transmitter of the external pacer. The stimulating electrode set 21 can be used in combination with additional pacing electrodes, as are known in the art, to treat disorders of gastrointestinal motility. One device may control more than one set of sensing and/or stimulating electrodes. It should be appreciated that the sensing electrodes can be implemented in any of the embodiments of this inventions, including those depicted in FIGS. 2-6.

Any of the stimulating or sensing electrode sets can be placed by conventional surgical, laproscopic, endoscopic radiological, or other minimally invasive surgical techniques to place the desired device or devices on or adjacent to or in communication with the structure with which it is to be associated. Conventional electrode stimulation devices may be used in the practice of this invention. The following patent documents are incorporated herein by reference: U.S. Pat. Nos. 5,423,872, 5,690,691, 5,836,994, 5,861,044, 6,901,295, and 6,041,258, PCT Application Nos. PCT/US98/10402, PCT/US00/09910, and PCT/US00/10154, and U.S. patent application Ser. Nos. 09/424,324, 09/640,201, and 09/713,556. The devices disclosed by these references may be used for the novel methods described herein, altered or varied as appropriate.

From the foregoing detailed description, it can be seen that the present invention provides a method and apparatus for electrical stimulation of the pancreatico-biliary system. The present invention is achieved by the placement of electrode sets in the pancreatico-biliary system in an arrangement that induce contractions of the part or whole of the pancreatico-biliary system due to electrical stimulation of the surrounding tissue and nerves. The electrical stimulus is applied by a pulse generator for periods of varying duration and varying frequency so as to produce the desired contractions. An evaluation of the physical effects induced by the proper operation of the present invention can be made by inspection with an ultrasound, CAT scan or MRI or by insertion of a manometery catheter to measure pressures in the bile duct, pancreatic duct or ampullary sphincter.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

I claim:

1. A method for treating obesity in a patient, comprising the steps of:
    arranging at least one electrode on at least one of a pancreas, a pancreatic duct, a pancreatic sphincter, a bile duct, a cystic duct, a gall bladder, a biliary sphincter, or autonomic nerves supplying the pancreas and the biliary system, and
    activating said electrode to provide an electrical stimulus thereto, wherein said electrical stimulus is configured to cause a dissociation between a timing of food passing through the intestinal lumen and a timing of at least one of pancreatic or biliary secretions and thereby cause or increase a disruption in said patient's digestion of food.

2. The method of claim 1 wherein said electrical stimulus modulates the secretion of pancreatic juices into the small intestine.

3. The method of claim 1 wherein said electrical stimulus modulates the secretion of bile juices into the small intestine.

4. The method of claim 1 wherein said electrical stimulus causes contraction of at least one of the pancreas, the pancreatic duct, the pancreatic sphincter, the bile duct, the cystic duct, the gall bladder, or the biliary sphincter.

5. The method of claim 1 wherein said electrical stimulus relaxes at least one of the pancreas, the pancreatic duct, the pancreatic sphincter, the bile duct, the cystic duct, the gall bladder, or the biliary sphincter.

6. The method of claim 1 wherein said electrical stimulus increases tone of at least one of the pancreas, the pancreatic duct, the pancreatic sphincter, the bile duct, the gall bladder, or the biliary sphincter.

7. The method according to claim 1 wherein the electrical stimulus is provided by a pulse generator.

8. The method according to claim 7 wherein the electrical stimulus has a frequency in the range of approximately of 1 mHz to 1 MHz.

9. The method of claim 1, further incorporating the step of arranging at least one sensing electrode to detect a change in one or more physiological parameters.

10. The method of claim 9 wherein the physiological parameter is selected from the group consisting of esophageal peristalsis, esophageal pH, esophageal impedence, esophageal pressure, esophageal electrical activity, LES pressure, LES electrical activity, gastric peristalsis, gastric electrical activity, gastric chemical activity, gastric hormonal activity, gastric temperature, gastric pressure, gastric impedence, gastric pH, duodenal peristalsis, duodenal electrical activity, duodenal chemical activity, duodenal hormonal activity, duodenal temperature, duodenal pressure, duodenal impedence, duodenal pH, blood activity, chemical activity, hormonal activity, vagal activity, gastrointestinal neural activity, salivary chemical activity, biliary pressure, biliary electrical activity, biliary chemical activity, pancreatic pressure, pancreatic electrical activity, pancreatic chemical activity, pancreatic sphincter pressure, pancreatic sphincter electrical activity, biliary sphincter pressure, and biliary sphincter electrical activity.

11. A method for treating obesity in a patient, comprising the steps of:
    arranging at least one electrode on at least one of a pancreas, a pancreatic duct, a pancreatic sphincter, a bile duct, a cystic duct, a gall bladder, or a biliary sphincter; and
    activating said electrode to provide an electrical stimulus thereto, wherein said electrical stimulus is effective to inhibit at least one of fat digestion or fat absorption by said patient.

12. The method of claim 11 wherein said electrical stimulus modulates the secretion of pancreatic juices into the small intestine.

13. The method of claim 11 wherein said electrical stimulus modulates the secretion of bile juices into the small intestine.

14. The method of claim 11 wherein said electrical stimulus causes contraction of at least one of the pancreas, the pancreatic duct, the pancreatic sphincter, the bile duct, the cystic duct, the gall bladder, or the biliary sphincter.

15. The method according to claim 11 wherein the electrical stimulus is provided by a pulse generator.

16. The method according to claim 15 wherein the electrical stimulus has a frequency in the range of approximately of 1 mHz to 1 MHz and a power range of 1 mAmp to 10 Amp.

17. The method of claim 11, further incorporating the step of arranging at least one sensing electrode to detect a change in one or more physiological parameters.

18. The method of claim 17 wherein the physiological parameter is selected from the group consisting of esophageal peristalsis, esophageal pH, esophageal impedence, esophageal pressure, esophageal electrical activity, LES pressure, LES electrical activity, gastric peristalsis, gastric electrical activity, gastric chemical activity, gastric hormonal activity, gastric temperature, gastric pressure, gastric impedence, gastric pH, duodenal peristalsis, duodenal electrical activity, duodenal chemical activity, duodenal hormonal activity, duodenal temperature, duodenal pressure, duodenal impedence, duodenal pH, blood activity, chemical activity, hormonal activity, vagal activity, gastrointestinal neural activity, salivary chemical activity, biliary pressure, biliary electrical activity, biliary chemical activity, pancreatic pressure, pancreatic electrical activity, pancreatic chemical activity, pancreatic sphincter pressure, pancreatic sphincter electrical activity, biliary sphincter pressure, and biliary sphincter electrical activity.

19. The method of claim 11 wherein said electrical stimulus increases tone of at least one of the pancreas, the pancreatic duct, the pancreatic sphincter, the bile duct, the cystic duct, the gall bladder, or the biliary sphincter.

20. A device for electrical stimulation, comprising:
a pulse generator; and
at least one electrode connected to the pulse generator wherein the electrode is arranged on at least one of a patient's pancreas, pancreatic duct, pancreatic sphincter, bile duct, gall bladder, biliary sphincter, or autonomic nerves supplying the pancreas, such that activating said electrode is effective to treat obesity in said patient by delivering an electrical stimulus configured to cause a dissociation between a timing of food passing through the intestinal lumen and a timing of at least one of pancreatic or biliary secretions and thereby causing or increasing an inhibition of at least one of fat digestion or fat absorption in said patient.

* * * * *